US00PP35282P2

(12) United States Plant Patent
Trees

(10) Patent No.: US PP35,282 P2
(45) Date of Patent: Jul. 25, 2023

(54) ***LANTANA* PLANT NAMED 'BALUCYELI24'**

(50) Latin Name: *Latana camara*
Varietal Denomination: Balucyeli24

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/099,705

(22) Filed: Jan. 20, 2023

(51) Int. Cl.
*A01H 5/00* (2018.01)
*A01H 6/00* (2018.01)

(52) U.S. Cl.
USPC ..... Plt./227

(58) Field of Classification Search
USPC ..... Plt./226, 227
See application file for complete search history.

(56) References Cited

U.S. PATENT DOCUMENTS

PP17,625 P2 * 4/2007 Trees ..... A01H 6/00
Plt./227

* cited by examiner

*Primary Examiner* — Karen M Redden
(74) *Attorney, Agent, or Firm* — Audrey Charles

(57) ABSTRACT

A new and distinct cultivar of *Lantana* plant named 'Balucyeli24', characterized by its deep yellow-colored inflorescences, dark green-colored foliage, and moderately vigorous, mounded-spreading growth habit, is disclosed.

1 Drawing Sheet

Latin name of genus and species of plant claimed: *Lantana camara.*

Variety denomination: 'Balucyeli24'.

BACKGROUND OF THE INVENTION

The present invention relates to a new and distinct cultivar of *Lantana* plant botanically known as *Lantana camara* and hereinafter referred to by the cultivar name 'Balucyeli24'.

The new cultivar originated in a controlled breeding program in Guadalupe, Calif. during June 2019. The objective of the breeding program was the development of *Lantana* cultivars have attractive flower coloration, dark green foliage, and a moderately vigorous, mounded-spreading growth habit.

The new *Lantana* cultivar is the result of cross-pollination. The female (seed) parent of the new cultivar is the proprietary *Lantana camara* breeding selection coded 19299, not patented, characterized by its medium yellow-colored inflorescences, dark green-colored foliage, low growth vigor and semi-upright growth habit. The male (pollen) parent of the new cultivar is the proprietary *Lantana camara* breeding selection coded 3930-A, not patented, characterized by its medium yellow and orange colored inflorescences, dark green-colored foliage, low growth vigor and semi-upright growth habit. The new cultivar was selected as a single flowering plant within the progeny of the above stated cross-pollination during April 2020 in a controlled environment in Guadalupe, Calif.

Asexual reproduction of the new cultivar by terminal stem cuttings since April 2020 in Guadalupe, Calif. and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balucyeli24' as a new and distinct cultivar of *Lantana* plant:

1. Deep yellow-colored inflorescences;
2. Dark green-colored foliage; and
3. Moderately vigorous, mounded-spreading growth habit.

Plants of the new cultivar differ from plants of the female parent primarily in having more inflorescences per plant, increased growth vigor and a mounded-spreading growth habit unlike the semi-upright growth habit of the female parent. Plants of the new cultivar differ from plants of the male parent primarily in having increased growth vigor, deep yellow-colored inflorescences and a mounded-spreading growth habit unlike the medium yellow and orange colored inflorescences and the semi-upright growth habit of the male parent.

Of the many commercially available *Lantana* cultivars, the most similar in comparison to the new cultivar is Lucky Pot of Gold 'Balucgold', U.S. Plant Pat. No. 14,634. However, in side-by-side comparisons, plants of the new cultivar differ from plants of 'Balucgold' in at least the following characteristics:

1. Plants of the new cultivar have fewer flowers per inflorescence than plants of 'Balucgold';
2. Plants of the new cultivar have a yellow petal color different from the yellow-orange petal color of plants of 'Balucgold'; and 3. Plants of the new cultivar have a more mounded-spreading growth habit than plants of 'Balucgold'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balucyeli24'. The plants were approximately 5-months old. The plants were grown in twelve inch hanging baskets for approximately 11 weeks in an outdoor nursery in West Chicago, Ill. Plants were given three pinches prior to transplant and one application of Daminozide at 2500 ppm after the first pinch.

DETAILED BOTANICAL DESCRIPTION

Figure 1:
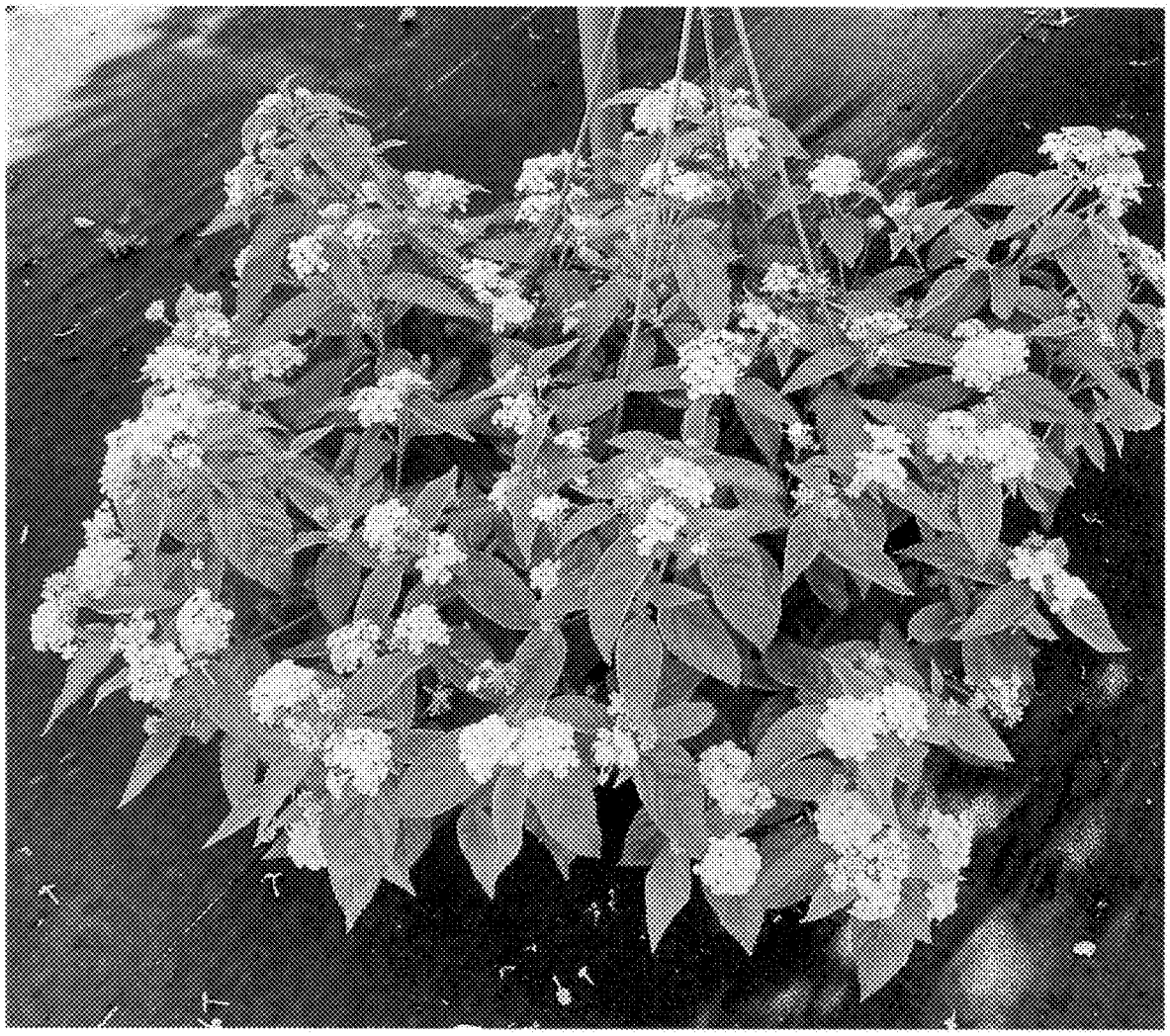
FIG. 1 illustrates a side view of the overall growth and flowering habit of 'Balucyeli24'.
Figure 2:
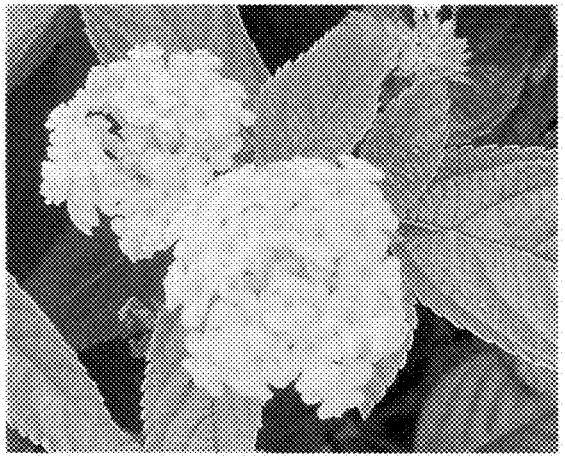
FIG. 2 illustrates a close-up view of the inflorescences of 'Balucyeli24'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2022 under natural light conditions in Naperville, Ill.

The following descriptions and measurements describe approximately 5-month-old plants produced from cuttings from stock plants and grown under conditions comparable to those used in commercial practice. The plants were grown in twelve inch hanging baskets for approximately 11 weeks in an outdoor nursery in West Chicago, Ill. Plants were given three pinches prior to transplant and one application of Daminozide at 2500 ppm after the first pinch. Prior to transplant plants were grown in a polycarbonate greenhouse in West Chicago, Ill. Greenhouse temperatures were maintained at approximately 75° F. to 80° F. (24° C. to 27° C.) during the day and approximately 65° F. to 70° F. (18° C. to 21° C.) during the night. Supplemental lighting was used for first four weeks after sticking. Measurements and numerical values represent averages of typical plants.

Botanical classification: *Lantana camara* 'Balucyeli24'.

Parentage:

*Female parent.*—Proprietary *Lantana camara* breeding selection coded 19299, not patented.

*Male parent.*—Proprietary *Lantana camara* breeding selection coded 3930-A, not patented.

Propagation:

*Type cutting.*—Terminal stem.

*Time to initiate roots.*—Approximately 7 to 11 days.

*Time to produce a rooted cutting.*—Approximately 28 to 35 days.

*Root description.*—Fibrous.

*Rooting habit.*—Freely branching.

Plant description:

*Commercial crop time.*—Approximately 6 to 7 weeks from a rooted cutting to finish in a 10 cm container.

*Growth habit and general appearance.*—Moderately vigorous, mounded-spreading.

*Size.*—Height from soil level to top of plant plane: Approximately 32.0 cm. Width: Approximately 67.0 cm.

*Branching habit.*—Freely branching, pinching enhances branching. Quantity of branches per plant: Approximately 3 basal branches with 6 main lateral branches.

*Lateral branch.*—Shape: Square in cross section. Strength: Strong, becomes woody with age. Length: Approximately 33.0 cm. Diameter: Approximately 4.0 mm. Length of central internode: Approximately 3.0 cm. Texture: Densely pubescent with a mixture of glandular and nonglandular hairs. Gland color: Colorless, transparent. Color of young stem: 146B to 146C. Color of mature stem: 146B, becomes woody 199A to 199B with age.

Foliage description:

*General description.*—Quantity of leaves per lateral branch: Approximately 16. Fragrance: Strong, spicy. Form: Simple. Arrangement: Opposite.

*Leaves.*—Aspect: Perpendicular to obtuse angle to stem. Shape: Ovate. Margin: Serrate. Apex: Acute. Base: Obtuse. Venation pattern: Pinnate. Length of mature leaf: Approximately 6.6 cm. Width of mature leaf: Approximately 3.2 cm. Texture of upper surface: Moderately scabrous. Texture of lower surface: Densely pubescent with a mixture of scabrous and glandular hairs. Gland color: Colorless, transparent. Color of upper surface of young foliage: Closest to 137A with venation of 146B to indistinguishable. Color of lower surface of young and mature foliage: Closest to 147B with venation of 146C. Color of upper surface of mature foliage: Closest to 137A with NN137A and venation of 146B to indistinguishable.

*Petiole.*—Length: Approximately 1.1 cm. Diameter: Approximately 2.0 mm. Texture: Moderately pubescent with a mixture of scabrous and glandular hairs. Gland color: Colorless, transparent. Color: 146B.

Flowering description:

*Flowering habit.*—'Balucyeli24' is freely flowering under outdoor growing conditions with substantially continuous blooming from spring through autumn and year-round in greenhouse environment.

*Lastingness of individual inflorescence on the plant.*—Approximately 2 to 3 weeks.

Inflorescence description:

*General description.*—Type: Hemispherical head, axillary or terminal. Quantity per plant: Approximately 64. Fragrance: Strong, spicy. Aspect: Primarily facing upward or outward. Height: Approximately 2.0 cm. Width: Approximately 3.5 cm. Quantity of fully open flowers per inflorescence: Approximately 30.

*Peduncle.*—Strength: Strong. Shape: Square in cross section. Aspect: Acute angle to stem. Length: Approximately 3.0 cm to 4.0 cm. Diameter: Approximately 2.0 mm. Texture: Densely pubescent with a mixture of glandular and nonglandular hairs. Gland color: Colorless, transparent. Color: 146B.

Flower description:

*General description.*—Type: Salverform.

*Bud.*—Rate of opening: Generally takes 1 to 2 days for bud to progress from first color to fully open flower.

Buds open in progression from the margin to the center of the inflorescence. Quantity of unopened inflorescences per plant: Approximately 60.

*Bud just before opening.*—Shape: Elongated, rectangular at apex. Length: Approximately 1.1 cm. Diameter: Approximately 3.0 mm. Color: 13C.

*Corolla.*—Depth: Approximately 1.6 cm. Diameter: Approximately 1.0 cm.

*Petals.*—Quantity: 4, non-imbricate, non-symmetrical petals. Petals are fused at base forming a corolla tube. Shape: Obovate. Appearance: Matte. Aspect: Flat to cupped. Margin: Entire, ruffled. Apex: Obtuse. Length of upper petal from throat: Approximately 4.0 mm. Width of upper petal: Approximately 7.0 mm. Length of lateral petals from throat: Approximately 4.0 mm. Width of lateral petals: Approximately 4.0 mm. Length of lower petal from throat: Approximately 5.0 mm. Width of lower petal: Approximately 6.0 mm. Texture of upper surface: Glabrous. Texture of lower surface: Densely pubescent. Color of upper surface when first open: 13A. Color of lower surface when first open: 13C. Color of upper surface when fully open: 13A, fading to 13B with age. Color of lower surface when fully open: 13D.

*Corolla tube.*—Length: Approximately 1.1 cm. Diameter at tube opening: Approximately 1.0 mm. Diameter at base: Approximately 1.0 mm. Texture of inner surface: Sparsely pubescent. Texture of outer surface: Densely pubescent at tube opening transitioning to glabrous at base. Color of pubescence 13C. Color of inner surface: 13D. Color of outer surface: 13D with base of 145D.

*Calyx.*—Shape: Tubular with two broadly acute tips. Length: Approximately 3.0 mm. Diameter: Approximately 2.0 mm. Texture of inner surface: Glabrous. Texture of outer surface: Densely pubescent. Color of inner and outer surfaces: 145D.

*Bracts.*—Quantity per flower: 1 per flower. Shape: Lanceolate. Length: Approximately 6.0 mm. Width: Approximately 1.0 mm. Texture of upper surface: Sparsely pubescent. Texture of lower surface: Densely pubescent. Color of upper surface: 146B with base of 145D. Color of lower surface: 146C with base of 145D.

*Reproductive organs.*—Androecium: Stamen quantity: 4, adnate to corolla tube. Stamen length: Approximately 2.0 mm. Anther shape: Bilobed, ovoid. Anther length: Approximately 1.0 mm. Anther color: 8A. Pollen amount: Abundant. Pollen color: 8D. Gynoecium: Pistil quantity: 1 per flower. Pistil length: Approximately 3.0 mm. Stigma shape: Funnel. Stigma length: Less than 1.0 mm. Stigma color: 145A. Style length: Approximately 2.0 mm. Style color: 155D, translucent. Ovary diameter: Approximately 1.0 mm. Ovary color: 144D.

Seed and fruit production: Neither seed nor fruit production has been observed.

Disease and pest resistance: Resistance to pathogens and pests common to *Lantana* has not been observed.

What is claimed is:

1. A new and distinct cultivar of *Lantana* plant named 'Balucyeli24', substantially as herein illustrated and described.

* * * * *